(12) United States Patent
Chen et al.

(10) Patent No.: US 9,012,512 B2
(45) Date of Patent: Apr. 21, 2015

(54) AQUEOUS EXTRACTS FROM MONOCOTYLEDON PLANTS AND THEIR USE IN CARDIOPROTECTION

(75) Inventors: Shui-Tein Chen, Taipei (TW); Jung-Feng Hsieh, Taipei (TW)

(73) Assignee: Academia Sinica, Taipei (TW)

( * ) Notice: Subject to any disclaimer, the term of this patent is extended or adjusted under 35 U.S.C. 154(b) by 934 days.

(21) Appl. No.: 12/428,551

(22) Filed: Apr. 23, 2009

(65) Prior Publication Data

US 2009/0298945 A1 Dec. 3, 2009

Related U.S. Application Data

(60) Provisional application No. 61/047,839, filed on Apr. 25, 2008.

(51) Int. Cl.
*A61K 31/194* (2006.01)

(52) U.S. Cl.
CPC ........................... *A61K 31/194* (2013.01)

(58) Field of Classification Search
CPC ....................................................... A61K 31/194
USPC ........................................ 424/725; 514/675
See application file for complete search history.

(56) References Cited

U.S. PATENT DOCUMENTS

| | | | | |
|---|---|---|---|---|
| 2004/0022880 | A1* | 2/2004 | Shi | 424/764 |
| 2006/0057073 | A1* | 3/2006 | Lintz et al. | 424/45 |
| 2008/0089957 | A1* | 4/2008 | Chen et al. | 424/725 |

OTHER PUBLICATIONS

Hagiwara et al., JP 62259570, 1987, Abstract Only.*
Bestman-Smith et al., Sodium Lauryl Sulfate Abrogates Human Immunodeficiency Virus Infectivity by Affecting Viral Attachment, 2001, Antimicrobial Agents and Chemotherapy, vol. 45, No. 8, pp. 2229-2237.*
Ahmad et al., "Phenolic glycosides from *Symplocos racemosa*: Natural Inhibitors of Phosphodiesterase I," *Phytochemistry*, 63:217-220 (2003).
Das, Shankar B. and Rajemdra K. Sharma, "Potential Role of Calmodulin-Dependent Phosphodiesterase in Human Brain Tumor," *Oncology Reports*, 14:1059-1063 (2005).
Hourani et al., "Role of Cyclic Nucleotides in Vasodilations of the Rat Thoracic Aorta Induced by Adenosine Analogues," *British Journal of Pharmacology*, 133:833-840 (2001).
Omori, Kenji and Jun Kotera, "Overview of ODEs and Their Regulation," *Circ. Res.* 100:309-327 (2007).
Travadi, J.N. and S.K. Patole, "Phosphodiesterase Inhibitors for Persistent Pulmonary Hypertension of the Newborn: A Review," *Pediatric Pulmonology*, 36:529-535 (2003).

Fields et al., "Allopurinol an Inhibitor of Xanthine Oxidase Reduces Uric Acid Levels and Modifies the Signs Associated with Copper Deficiency in Rats Fed Fructose", Free Radical Biology & Medicine, vol. 20, No. 4, pp. 595-600 (1996).
Fernandes et al., "2-Styrylchromones As Novel Inhibitors of Xanthine Oxidase A Structure-activity Study", Journal of Enzyme Inhibition and Medicinal Chemistry, vol. 17 (1), pp. 45-48 (2001).
Goldstein et al., "Oral Sildenafil in the Treatment of Erectile Dysfunction", The New England Journal of Medicine, vol. 338, No. 20 (1998).
Henderson et al.,"The Metabolism of 4-Aminopyrazolo (3,4-d)pyrimidine in Normal and Neoplastic Tissue," Cancer Research 21:118-129 (1961).
Kar et al., "Experimental Visceral Leishmaniasis Role of Trans-aconitic Acid in Combined Chemotherapy", Antimicrobial Agents and Chemotherapy, vol. 37, No. 11, pp. 2459-2465 (1993).
Kong et al., "Inhibition of Xanthine Oxidase by Liquiritigenin and Isoliquiritigenin Isolated from Sinofranchetia Chinensis", CMLS Cellular and Molecular Life Sciences, vol. 57 (2000).
Mamillapalli et al., "Enhancement and Inhibition of Snake Venom Phosphodiesterase Activity by Lysophospholipids", FEBS Letters 436, pp. 256-258 (1998).
Nguyen et al., "Xanthine Oxidase Inhibitory Activity of Vietnamese Medicinal Plants", Biol. Pharm. Bull. 27 (9) 1414-1421 (2004).
O'Driscoll et al., "Nitric Oxide-Dependent Endothelial Function is Unaffected by Allopurinol in Hypercholesterolaemic Subjects," Clinical and Experimental Pharamacology and Physiology, 26:779-783 (1999).
Tamta et al., "6-(N-benzoylamino)Purine as a Novel and Potent Inhibitor of Xanthine Oxidase Inhibition Mechanism and Molecular Modeling Studies", Journal of Enzyme Inhibition and Medicinal Chemistry, 20(4), pp. 317-324 (2005).
Tamta et al., "Biochemical Characterization of Some Pyrazolopyrimidine-Based Inhibitors of Xanthine Oxidase", Biochemistry (Moscow), vol. 71, pp. S49-S54 (2006).
Wang et al., "The vasorelaxing Action of Rutaecarpine Direct Paradoxical Effects on Intracellular Calcium Concentration of Vascular Smooth Muscle and Endothelial Cells", The Journal of Pharmacology and Experimental Therapeutics, vol. 276, No. 3, pp. 1016-1021 (1996).
Wang et al., "Vasorelaxing Action of Rutaecarpine Effects of Rutaecarpine on Calcium Channel Activities in Vascular Endothelial and Smooth Muscle Cells", The Journal of Pharmacology and Experimental Therapeutics, vol. 289, No. 3, pp. 1237-1244 (1999).
Williams et al., "Kinetic and E.P.R. Studies on the Inhibition of Xanthine Oxidase by Alloxanthine (1H-pyrazolo[3,4-dipyrimidine-4,6-diol)," Biochem. J. 195:753-760 (1981).

* cited by examiner

*Primary Examiner* — James D Anderson
*Assistant Examiner* — Meghan Finn
(74) *Attorney, Agent, or Firm* — Wolf, Greenfield & Sacks, P.C.

(57) ABSTRACT

Method of treating hypertension with a trans-aconitic acid containing composition (e.g., a water extract derived from a monocotyledon plant).

5 Claims, 1 Drawing Sheet

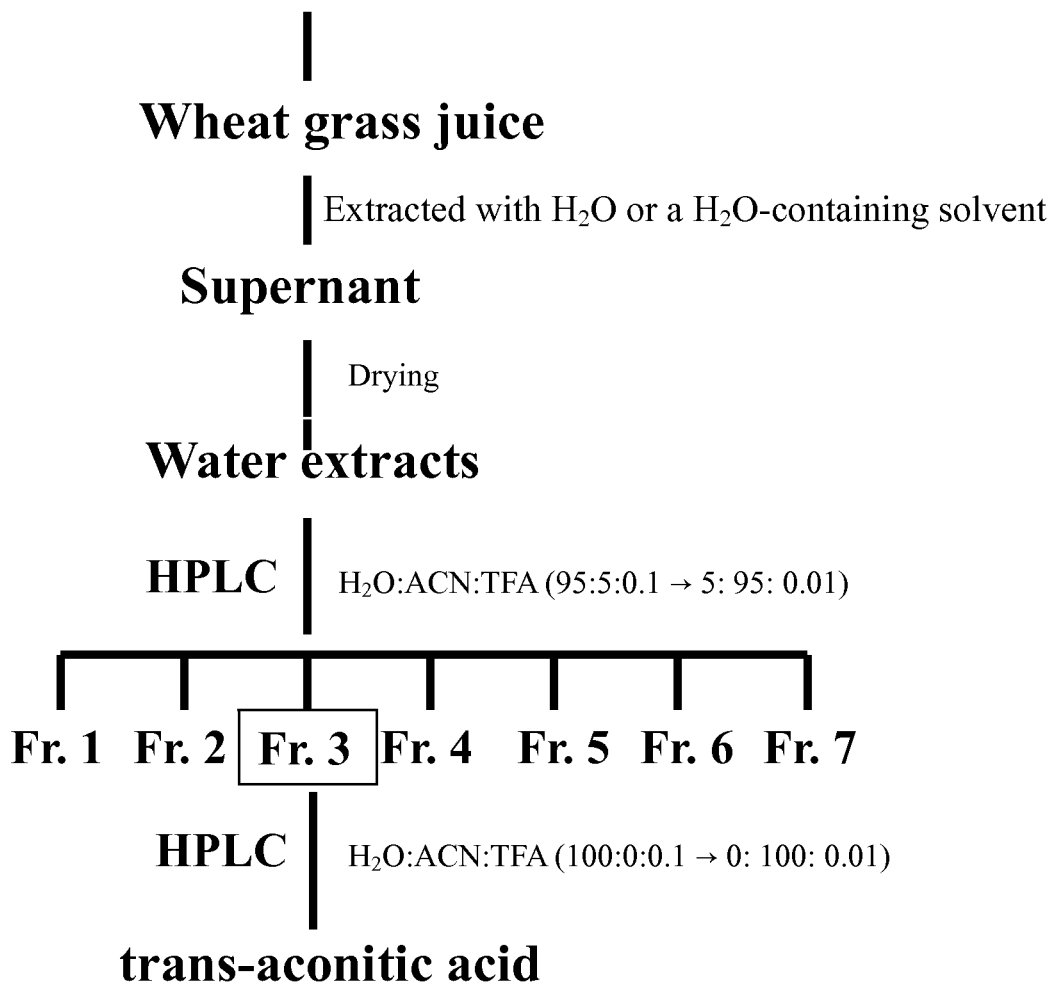

AQUEOUS EXTRACTS FROM MONOCOTYLEDON PLANTS AND THEIR USE IN CARDIOPROTECTION

RELATED APPLICATION

This application claims priority to U.S. Provisional Application No. 61/047,839, filed on Apr. 25, 2008, the content of which is hereby incorporated by reference in its entirety.

BACKGROUND OF THE INVENTION

Monocotyledon plants are important agriculture plants having great economic values. Among them, wheat is one of the most important cereal crops in the world. Its consumption has doubled in the past 30 years to nearly 600 million tons per year and, according to the International Maize and Wheat Improvement Center, will increase over 40% by 2020.

Wheat, as well as many other monocotyledon plants, have been used to make a variety of food products, such as bread, cookies, cakes, crackers, and noodles. In addition, it is also of great interest to identify bioactive molecules contained in monocotyledon plants for pharmaceutical uses.

SUMMARY OF THE INVENTION

This invention is based on the unexpected discovery that trans-aconitic acid (TAA), a component contained in all monocotyledon plants, exhibits vasorelaxing effect, an underline mechanism for hypertension treatment.

Accordingly, this invention provides a method of treating hypertension by administering to a subject in need of the treatment an effective amount of a composition (e.g., an aqueous extract of a monocotyledon plant) containing TAA. The term "treating" as used herein refers to the application or administration of a composition including active agents to a subject, who has hypertension, a symptom of hypertension, or a predisposition toward hypertension, with the purpose to cure, heal, alleviate, relieve, alter, remedy, ameliorate, improve, or affect hypertension, the symptoms of hypertension, or the predisposition toward hypertension. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

When a monocotyledon plant aqueous extract is used in the method of this invention, it can be prepared by extracting a part (e.g., leaf) of the plant (e.g., a crop) with water to obtain an aqueous solution and then drying the solution to produce the water extract in dried form. Examples of crops include, but are not limited to, wheat, rice, Japanese silvergrass, Chinese pennisetum, sorghum, and millet.

The TAA-containing composition described above can be used together with glyceryltrinitrate (GTN) or sodium nitroprusside (SNP) for treating hypertension or relaxing vascular contraction. It also can be used for the manufacture of a medicament for the same purposes.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The drawings are first described.

FIG. 1 is a flowchart showing procedures of preparing a water extract from leaves of wheat (*Triticum aestivum* L.) and the fractionation thereof to identify TAA.

DETAILED DESCRIPTION OF THE INVENTION

Described herein is a method of using a TAA-containing composition for relaxing vascular contraction and treating hypertension. This TAA-containing composition can be a water extract prepared from a monocotyledon plant, i.e., a plant having one cotyledon, or embryonic leaf, in its seeds. Preferably, the monocotyledon plant is a crop, which refers to a plant grown in significant quantities to be harvested as food, livestock fodder, or any other economic purposes. A water extract of a plant can be prepared by soaking a part of the plant (e.g., leaf, root, seed, flower, or tuber) in a suitable amount of pure water or a water-containing solvent for a suitable period of time (e.g., 5 minutes to an hour) at a suitable temperature (e.g., 60° C. to 90° C.) and then collecting the water-soluble fraction thus formed, which can be dried by, e.g., spray drying or freeze-drying, subsequently to obtain a water extract in powder form. Chromatography or other methods known in the art can be applied to confirm the existence of TAA in the water extract thus prepared. Cardioprotection effects, such as relaxation of vascular contraction and lowering blood pressure, can be determined by both in vivo and in vitro studies as described herein or known in the art.

The TAA-containing composition described above is preferably mixed with a pharmaceutically acceptable carrier, and optionally, with GTN or SNP, to form a pharmaceutical composition. A pharmaceutically acceptable carrier is a carrier compatible with the active ingredient of the composition (and preferably, capable of stabilizing the active ingredient) and not deleterious to the subject to be treated. One or more solubilizing agents can be utilized as pharmaceutical excipients for delivery of the TAA-containing composition. Examples of other carriers include colloidal silicon oxide, magnesium stearate, cellulose, sodium lauryl sulfate, and D&C Yellow #10.

The pharmaceutical composition described above can be administered to a subject via a conventional route, e.g., parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having TAA and optionally, GTN or SNP, can also be administered in the form of suppositories for rectal administration.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

EXAMPLE 1

Preparation of a TAA-Containing Water Extract from Wheat

Common wheat (*Triticum aestivum* L.) was grown in a high container (30 cm diameter×15 cm height) at 18° C. to 24° C. and exposed to sun light (16 hours per day) for 10 days. 3660 g leaves of the wheat were then harvested and milled by a laboratory-scale milling machine. After removing pulps by filtration, the wheat sample thus collected was mixed with water and heated at 85° C. for 10 min. After 15 min of centrifugation at 12,000 g, the resultant supernatant (2.2 L) was collected and freeze-dried to yield 98 g water extract of wheat, which was stored at −80° C. before use.

20.0 g of the wheat extract described above was subjected to HPLC chromatography to obtain seven fractions (Fr.), each at elution time of 0-4, 4-6.5, 6.5-10, 10-19, 19-23, 23-41, or 41-59 min. The total yield of the seven fractions was 87.1%, while the yield of each fraction was 14.7, 18.1, 21.3, 4.9, 3.8, 17.2, or 7.1%.

Fraction 3 (4.26 g) was then undergone HPLC chromatography again to obtain a fraction containing a pure compound. The total yield of this compound was 2.3% (97.9 mg). The compound was then analyzed using a high-resolution ESI-TOF mass spectrometer (BioTOF III; Bruker Daltonics, Inc. Billerica, Mass., USA). NMR spectra of this compound in $D_2O$ were recorded on the Bruker Avance 400 spectrometer at 300 K, with standard pulse sequences provided by Bruker. Results thus obtained indicate that the compound is TAA, the chemical structure and physical features of which are shown below:

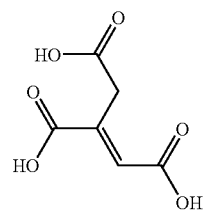

trans-Aconitic acid
$C_6H_6O_6$
Exact Mass: 174.0164
Mol. Wt.: 174.1082
m/e: 174.0164 (100.0%), 175.198 (6.5%), 176.0207 (1.2%)
C, 41.39; H, 3.47; O, 55.14

EXAMPLE 2

Vasorelaxing Effects of TAA on Phenylephrine-Induced Contraction

Male Sprague-Dawley rats, weighing 250-350 g (Laboratory Animal Science Center of the National Yang-Ming University, Taipei, Taiwan), were used in this study. The rats were allowed to acclimate in environmentally controlled quarters (20-22° C. with 12:12 hr light-dark cycles). Thoracic aorta was excised carefully and fixed isometrically in organ chambers (15 mL) containing a 37° C. modified Krebs' solution (120 mM NaCl, 4.5 mM KCl, 2.5 mM $CaCl_2$, 1 mM $MgSO_4$, 27 mM $NaHCO_3$, 1 mM $KH_2PO_4$, 10 mM glucose, pH 7.4) through which a mixture of 95% $O_2$-5% $CO_2$ was continuously supplied. The aortic rings of 3-4 mm were equilibrated under passive tension of 1.8 g for 60 min. After equilibration, the aortic rings were stabilized with a near maximal contraction induced by 0.3 μM phenylephrine. When the rings achieved a stable level of contraction, 3 μM acetylcholine was added to the bath, in which the aorta rings were soaked, to assess endothelial integrity. Intimas were gently frayed with a cotton swab to disrupt the endothelium. No acetylcholine-induced relaxation was observed, indicating that the vessels were successfully denuded.

The relaxant effect of trans-aconitic acid (TAA), glyceryl-trinitrate (GTN) or sodium nitroprusside (SNP) on 0.3 μM phenylephrine precontracted aortic rings was examined. When contraction had reached a steady-state after about 10 min (considered as 100%, and was defined as control), TAA at 10 and 100 μM), or a vehicle control was added and their vasorelaxing effects were examined.

At the concentrations of 100 μM, TAA showed a significant vasorelaxing effect in rat thoracic aorta. This effect was dose dependent. TAA also resulted in a concentration-dependent relaxation in phenylephrine-induced contraction in endothelium-intact preparations. When the vascular contraction was induced by 10 μM phenylephrine, the maximum relaxation induced by TAA (100 μM) was 40% (n=16).

The relaxation effect of TAA on rat thoracic aorta in the presence of acetylcholine was also investigated. Vascular contraction in rat aortic rings was induced by 0.3 μM phenylephrine as described above. Acetylcholine (3 μM) was added to the bath, in which the aortic rings were soaked, to assess endothelial integrity. When endothelial integrity was confirmed, TAA (0.1-100 μM) was added, resulting in significant increase of relaxation levels. For example, at the concentration of 100 μM, TAA increases relaxation at the level of 55% (n=16).

EXAMPLE 3

Combined Vasorelaxing Effects of TAA and Glyceryltrinitrate (GTN) or Sodium Nitroprusside (SNP)

Vascular contraction was induced by phenylephrine in rat thoracic aorta following the method described in Example 1. GTN or SNP alone at concentrations 0.01 and 0.1 µM, or combined with TAA at 100 µM, was administered to the rats and their vasorelaxing effects were examine. Phenylephrine-induced tension (g) decreased significantly in the presence of GTN, an anti-hypertension agent. More specifically, when 0.1 µM GTN was used, the phenylephrine-induced tension (g) was 1.3 g. much lower than that in the presence of a control vehicle (2.1 g). The phenylephrine-induced tension was even lower, i.e., less than 1.0 g, in the co-presence of 0.1 µM GTN and 100 µM TAA. Similar results were observed when using the combination of TAA and SNP, another anti-hypertension agent. When SNP (0.1 µM) alone was used, the phenylephrine-induced tension (g) of was 1.0 g. When both SNP (0.1 µM) and TAA (100 µM) were used, the tension lowered to less than 0.8 g.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of lowering blood pressure in a patient with hypertension, comprising administering to said patient a composition comprising trans-aconitic acid in an amount effective to lower blood pressure.

2. The method of claim 1, wherein the composition further comprises glyceryltrinitrate or sodium nitroprusside.

3. The method of claim 1, further comprising administering to the subject an effective amount of glyceryltrinitrate.

4. The method of claim 1, further comprising administering to the subject an effective amount of sodium nitroprusside.

5. The method of claim 1, wherein the composition is a pharmaceutical composition, which further comprises a pharmaceutically acceptable carrier.

* * * * *